United States Patent
Häfele et al.

[11] Patent Number: 5,926,213
[45] Date of Patent: Jul. 20, 1999

[54] DEVICE FOR CORRECTING THE TONE OF COLOR PICTURES RECORDED BY A VIDEO CAMERA

[75] Inventors: Ulrich Häfele, Oberderdingen; Michael Vögele, Kämpfelbach; Jean-Pierre Heinrichs, Bretten, all of Germany

[73] Assignee: Richard Wolf GmbH, Knittlingen, Germany

[21] Appl. No.: 08/694,736

[22] Filed: Aug. 9, 1996

[30] Foreign Application Priority Data

Aug. 10, 1995 [DE] Germany ............... 195 29 367

[51] Int. Cl.$^6$ ........................................ H04N 9/73
[52] U.S. Cl. .................... 348/223; 348/45; 348/649
[58] Field of Search ................... 348/222, 223, 348/224, 225, 234, 645, 649, 652, 672, 65, 71, 74, 29, 30, 655; 600/101; 606/45; H04N 7/18, 9/73

[56] References Cited

U.S. PATENT DOCUMENTS

| | | |
|---|---|---|
| 4,951,134 | 8/1990 | Nakasima et al. . |
| 5,111,281 | 5/1992 | Sekiguchi . |
| 5,574,513 | 11/1996 | Topper .................................. 348/652 |
| 5,677,741 | 10/1997 | Yui ........................................ 348/649 |

FOREIGN PATENT DOCUMENTS

3315636 A1  10/1984  Germany .

*Primary Examiner*—Tuan Ho
*Attorney, Agent, or Firm*—Panitch Schwarze Jacobs & Nadel, P.C.

[57] ABSTRACT

The invention relates to a device for correcting the tone of color pictures recorded by a video camera, in particular an endoscope camera. A control device, which may also be part of a digital video camera, comprises a memory for storing a table which indicates a characteristic adjusting curve for tone correction values. The control device may further comprise an interface for inputting one or more characteristic adjusting curves according to the field of application of the device according to the invention. A simple rotary transducer which is connected via a lead to a control device serves as the input medium for the tone correction. After activating an automatic white balancing by way of a key connected to the control device, the correction values lies at the white point. The white point is always located on the adjusting curve and serves as a starting point. On operation of the rotary transducer, the tone correction is activated, and the control device reads out the value of the characteristic adjusting curve corresponding to the position of the rotary transducer from the look-up table stored in the memory. The point located on the adjusting curve after carrying out the correction remains also after switching off the control device an is only set to zero on renewed white balancing.

7 Claims, 5 Drawing Sheets

DEVICE FOR CORRECTING THE TONE OF COLOR PICTURES RECORDED BY A VIDEO CAMERA

BACKGROUND OF THE INVENTION

The invention relates to a device for correcting the tone of color pictures recorded by a video camera, in particular an endoscope camera, according to the preamble of patent claim 1.

DESCRIPTION OF THE PRIOR ART

In the past the primary field of application of endoscopy was in diagnosis. In diagnosis the physician observes the hollow organ which is to be examined with the naked eye. The eye has a high brightness and color dynamic, which has the result that the attainable image quality with respect to the definition and color representation is almost entirely dependent on the endoscope employed.

In surgery however other requirements are required from an endoscopic system than in diagnosis. With a surgical operation, the picture of the operational field must be available to the whole operation team, since several persons carry out the operation work in cooperation.

It is not therefore sufficient to observe the operational field through an endoscope with the naked eye. For this reason a video camera is placed upon the proximal end of the endoscope or a video endoscope with a distally arranged CCD sensor is applied, so that the operational field can be represented on a monitor. The application of CCD cameras however resulted in few problems since a CCD sensor does not possess the dynamics, sensitivity and the spectral characteristics of the eye. This is of particular relevance where color representation is concerned. One must also strive for the possibility of optimizing the color representation from the point of view of the color deviations occurring in an endoscopic system.

With endoscopic examination of a hollow organ of the body, the endoscope is first inserted into the body cavity or hollow organ which is to be examined. Via optical fibers in the endoscope, illumination light reaches into the body cavity where it illuminates the hollow organ. In order to achieve a genuine color reproduction, the illumination light should not be spectrally influenced by the hollow organ. However it is just exactly this which occurs, according to the type of hollow organ. Part of the illumination light penetrates for example into the mucous membrane, which acts as an absorption filter. In this way, for its part, the mucous membrane acts as a spectral narrow band illumination source, since the penetrated illumination light is filtered and again radiated at the surface of the mucous memebrane and the object to be observed for its part is illuminated with red light.

This light absorption behaviour differs according to the hollow organ to be examined. In the region of the joints the light absorption behaviour is not significant, whilst in the stomach where mucous membranes which are heavily supplied with blood are to be found, a color displacement in the direction of red occurs. The strength of the displacement to red depends, given a certain organ, on the observation distance and the observation and illumination angle of the endoscope. The shorter the observation distance or the nearer the endoscope is to the mucous memebrane, the stronger the mucous membrane is shined through which leads to a stronger displacement to red. This color displacement which is specific to the application is however not taken into account by prior art video cameras.

The U.S. Pat. No. 5,111,281 describes a color correction device for a video endoscope, said device comprising means for determining a color quality of a color image signal and means for carrying out a dynamic color correction in a pixel manner. Due to the correction effected in the pixel manner, the known device is not in the position to differentiate between strong colors occurring point by point, in particular red, and color increases which concern the whole picture, which leads to the result that the known device also corrects color increases occurring point for point and thus has a bad color differentiation.

The U.S. Pat. No. 4,951,134 shows a device for tone correction for an endoscope video camera. With this known device with the help of an input keyboard inputted correction values for the colors blue and red are first converted into digital values and processed into correction values in a microprocessor, and the outputted digital correction values, converted into analogue values using a digital-analogue converter, are used in the form of these analogue values for correction the color signals R and B of the video camera. Furthermore a display is provided on the monitor which quantitatively displays the contents of the tone correction control, i.e. in the form of figures.

SUMMARY OF THE INVENTION

It is the object of the present invention to make possible a device for correcting the tone of color pictures recorded by an endoscope video camera such that the tone correction can be carried out individually but specific to the application using simple input means.

One device in which the above object is achieved is specified in patent claim 1. Preferred embodiment forms of this device are to be deduced from claims 2 to 8.

According to the invention at least one characteristic adjustment curve lying within the color triangle is or is to be stored in the memory of the control device, on which the user can carry out an individual tone correction in a positive defined range using a simple stop free transformer (incremental transducer) rotatable over 360°. After carrying out an automatic white balancing, the white point is situated at the origin of the co-ordinate system defining the color space and is then the starting point of the characteristic adjusting curve which can be scanned in both directions.

It is also possible to predetermine several adjusting curves on the manufacturer's side taking account of the data of the solid body video camera and the characteristic data of known endoscope light sources as well as also taking into account the medical field of application. Since a mathematical determination of the adjusting curves is not possible, it is the case here of essentially empirically determined characteristic adjusting curves. The control device comprises an interface for inputting the specific adjusting curves. These can then be selected in the so equipped apparatus for example according to the selected light source or according to the chosen medical field of application.

The adjusting curves are preferably stored in tabular form in the memory of the control device, and the control device reads the tabular values from the memory on the basis of the respective correction sizes inputted to the rotary transducer.

It is useful when the stored characteristic adjusting curves concern in each case the tone correction of only two basic colors (e.g. red and blue) and when the third basic color is then determined from the control device according to the additive color law on the basis of the tone correction for the two basic colors.

Apart from the transformer for inputting the respective tone correction, the device according to the invention comprises a key connected to the control device for automatic white balancing (AWB).

A further input means may be provided for selecting one of several stored characteristic adjusting curves.

BRIEF DESCRIPTION OF THE DRAWINGS

The invention is hereinafter described in more detail by one embodiment of the invention represented in the drawings. These show.

DETAILED DESCRIPTION OF THE PREFERRED EMBODIMENTS

For explaining the principle of the application specific tone correction according to the invention, a color space of a video camera is represented schematically as a color triangle, the corner points of which are indicated as R'(RED'), G'(GREEN') and B'(BLUE'). There has not yet occurred an automatic white balancing AWB, i.e. the central point of the color triangle indicated at W'(WHITE') does not lie at the origin W (WHITE) of the color triangle determined by the co-ordinate axes U and V.

Figure 2:
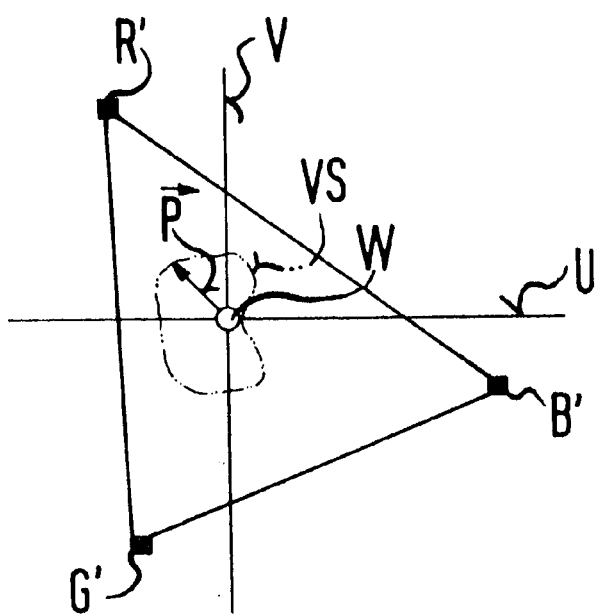

FIG. 2 shows the color space of a video camera after the white balancing has occurred. The central point of the color triangle lies at the origin of the co-ordinate system U, V. With the system specific tone correction according to the invention, the color triangle can now be vectorially guided with regard to the origin W of the nominal color space to a characteristic adjusting curve VS; the vector P indicates the adjusting curve VS. In the example shown the adjusting curve which is shown dashed is a closed two-dimensional curve.

Colors may be depicted by three independent parameters, generally by the three ground colors red green and blue. The color tone of a video picture therefore generally results from the color balance of the three ground colors red, green, and blue (R, G, B). With video cameras the ground color G ("green channel") represents the relative reference quantity, i.e. it remains constant relative to the ground colors red and blue. If one takes into account the additive characteristic of the colors, it is sufficient to adjust two of the three ground colors for the tone correction in order to represent each tone. It is therefore necessary to adjust only two independent parameters according to the dashed curve shown in FIG. 2. The suggested solution reduces this two dimensional procedue to a one dimensional operation using a stop free transformer which can be rotated about 360°.

Figure 3:
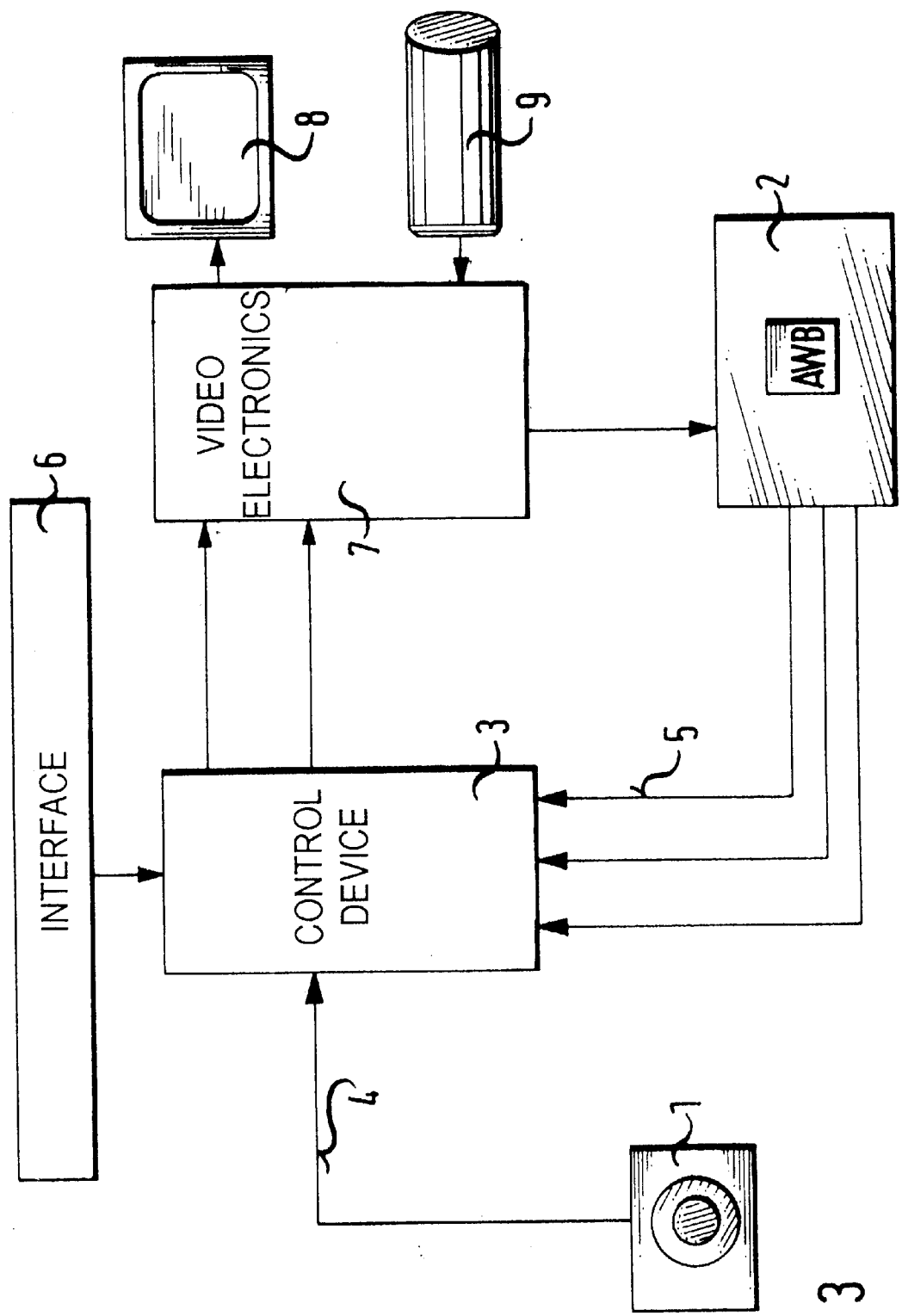

FIG. 3 shows the basic construction of a video camera containing a device according to the invention. A rotary transducer or transformer 1 for inputting the tone correction values and a key 2 for the automatic white balancing are connected via leads 4 and 5 to a control device 3 which comprises the memory for storing the characteristic adjusting curves. The rotary transducer as already mentioned is a stop free 360° transformer. An interface 6 is further connected to the control device 3 for inputting one or more characteristic adjusting curves.

The resulting red correction values and blue correction values determined by the control device are inputted to video electronics 7. The video electronics uses these values for setting the color balance (red, green, blue). A monitor 8 for displaying the endoscope picture recorded by the video camera and the picture converter 9 which is the recording part of the video camera is connected at the exit to the video electronics. The characteristic adjusting curves inputted via the interface 6 are first drawn up on the manufacturer's side taking account of the data of the solid body video camera and the characteristic data of known light sources and/or taking account of the medical application field such as urology, laparascopy, arthroscopy etc. and may be inputted via the interface 6, used for interfacing, individually or several at a time. As such, this concerns partly experimental values.

On the basis of the correction values inputted at the rotary transducer 1, the control device 3 carries out the tone correction on the basis of the stored characteristic adjusting curves in the form of a tabular control. With this, those correction values inputted at the transformer are advantageously converted into addresses for addressing the memory. The control device 3 may further comprise a microprocessor which carries out the tabular control. The adjusting range of the transformer, i.e. the exit values thereof may be quantisized and comprise for example 64 steps. The data specific to the manufacturer which indicates the characteristic adjusting curve each for the red part and the blue part may comprise seven bites plus a digit sign bite in the memory.

The tabular control then operates according to the following relations:

$red_{res}$=resulting red value $blue_{res}$=resulting blue value $red_{tab}$=tabular value red=f (Position of transformer characteristic adjusting curve)

$blue_{tab}$=tabular value blue=f (Position of transformer characteristic adjusting curve)

$red_{bas}$=basis value red=f (autom. white balancing)

$blue_{bas}$=basis value blue=f (autom. white balancing)

$red_{res}=red_{bas}+red_{tab}$ $blue_{res}=blue_{bas}+blue_{tab}$

Figure 4:
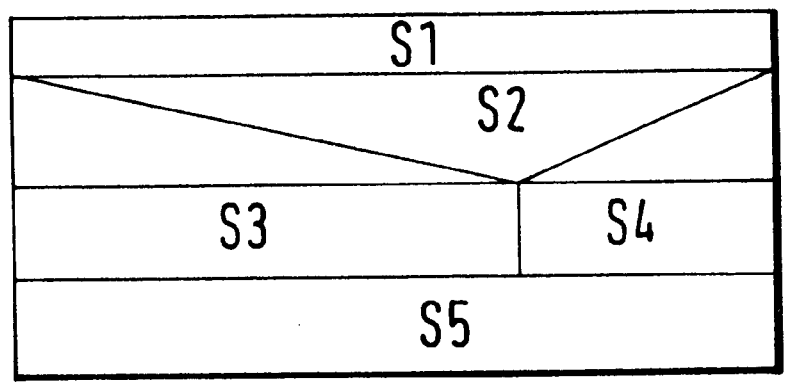

FIG. 4 shows the course of operation in the form of a flow diagram. At step S1 the camera is activated, step S2 enquires whether an automatic white balancing AWB is to be carried out or not. In the affirmative case the automatic white balancing is carried out and step S3 displaces the zero point of the color space into the center of the surface area of the color triangle spread by RED, GREEN, BLUE (FIG. 2). The momentary position of the transformer is allocated to the zero point W of the color space. By rotating the transformer, a two dimensional characteristic curve is traversed, e.g. the curve VS shown by a dashed line in FIG. 2.

Figure 1:
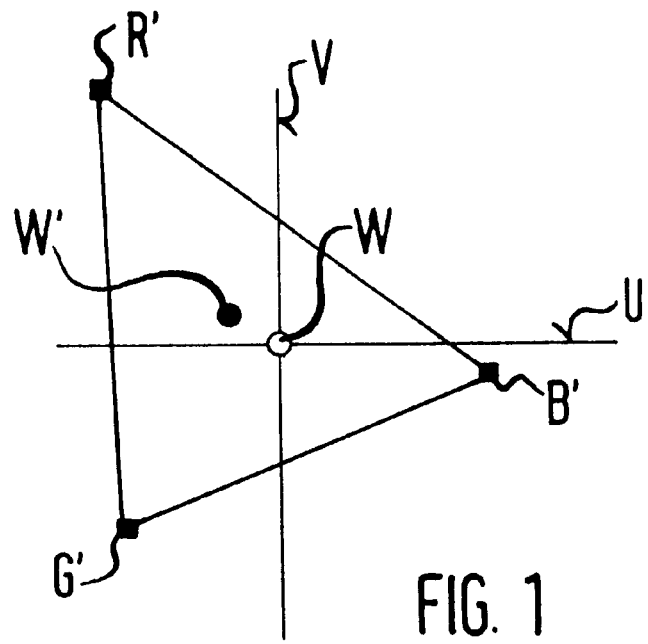
FIG. 1 schematically, a color space of a color video camera before automatic white balancing, FIG. 2 schematically, the color space of a color video camera after automatic white balancing with a characteristic adjusting curve, FIG. 3 a block diagram of one embodiment form of a device according to the invention for tone correction specific to the application, FIG. 4 a flow diagram of a control procedure with and without automatic white balancing, FIG. 5 a principle arrangement for determining characteristic adjusting curves and FIGS. 6A, 6B, 6C three examples of adjusting curves specific to the application.

Due to the tabular control which is then carried out, the control device determines the resulting values for the red correction and blue correction, and the video electronics determine the resulting tone using the additive color law and the green reference. If no automatic white balancing is carried out, step S4 confirms the old setting. In this case the origin W' of the color triangle is displaced with respect to the nominal origin W, as is shown in FIG. 1. A tone correction may however also be carried out in this case, whereby the characteristic adjusting curve however proceeds from point W', i.e. from the displaced origin. With each activation of the automatic white balancing AWB, those previously inputted and stored correction values are deleted and set to zero.

If, as mentioned above, a tone correction is activated without a prior automatic white balancing, there is no defined orientation point available to the user, the actual state of the correction is not displayed.

Since the process for carrying out the automatic color balancing is known, it is not described in any detail here. Principally however the procedure is such that the camera is aligned towards a well lit white object and the procedure AWB is activated. At the same time the camera electronics internally measure the intensity distribution in the three colors red, green and blue. The measurement value of the green channel is generally used as the reference value to which the both the other channels are adapted in a level manner with the help of a controllable amplifier. The control values for this amplifier form the basis data which are then computed with the correction values and finally give the resulting tone correction values.

Figure 5:
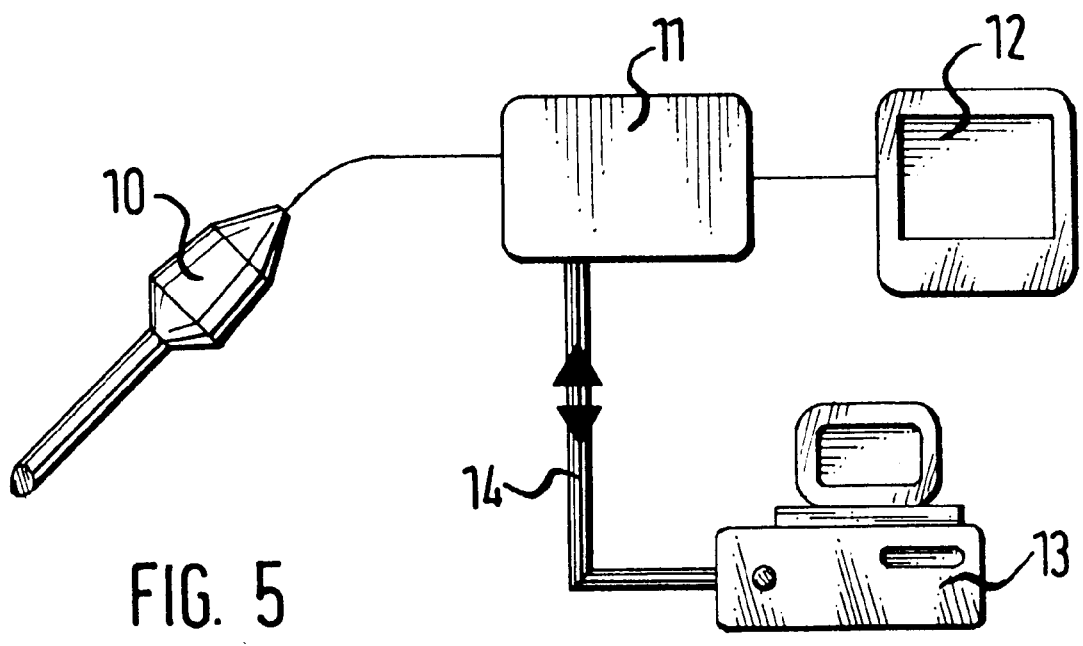

FIG. 5 shows the fundamental arrangement for determining one or more characteristic adjusting curves. A real operation site or a corresponding display specimen, according to the application, is illuminated with a light source and the object is recorded with an endoscope 10 which is connected to a video camera 11 and a monitor 12. The resulting characteristic adjusting curve is filed in the form of measurement values from the video camera 11 to a memory of a computer 13 via a data lead 14. Each recorded characteristic adjusting curve, apart from being dependent on the specific field of application, may also be dependent on the color temperature and of course also the subjective color sensitivity of the user. With this, those values filed in the computer which define the respective characteristic adjusting curve can be evaluated in the computer. After an adequate number of tests there results a correction table which for example is transferred during the production process in each control device of the camera.

Figure 6A:
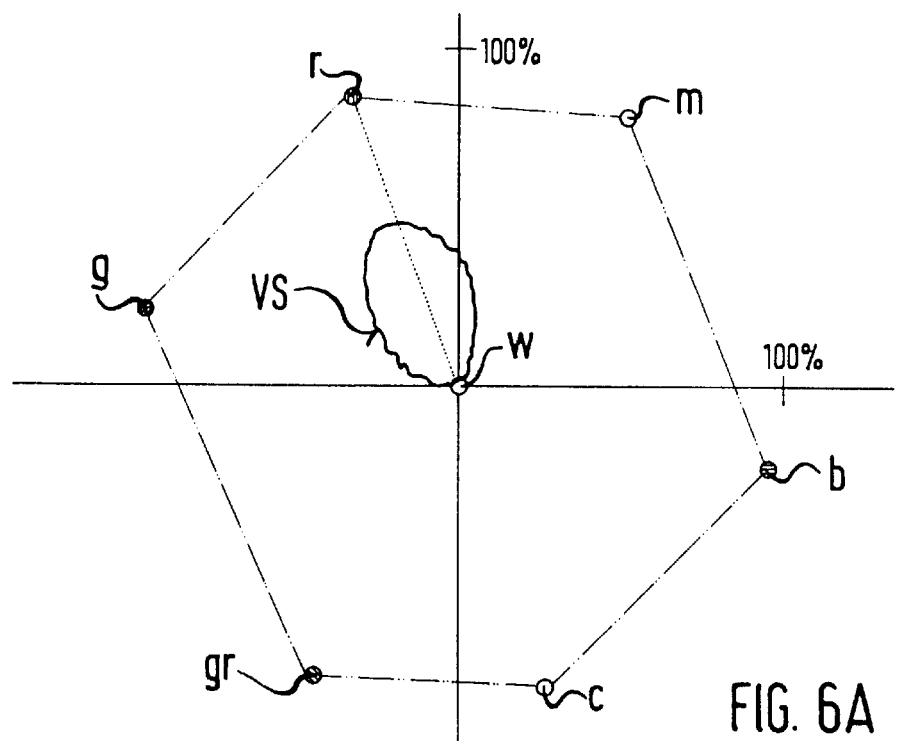
Figure 6B:
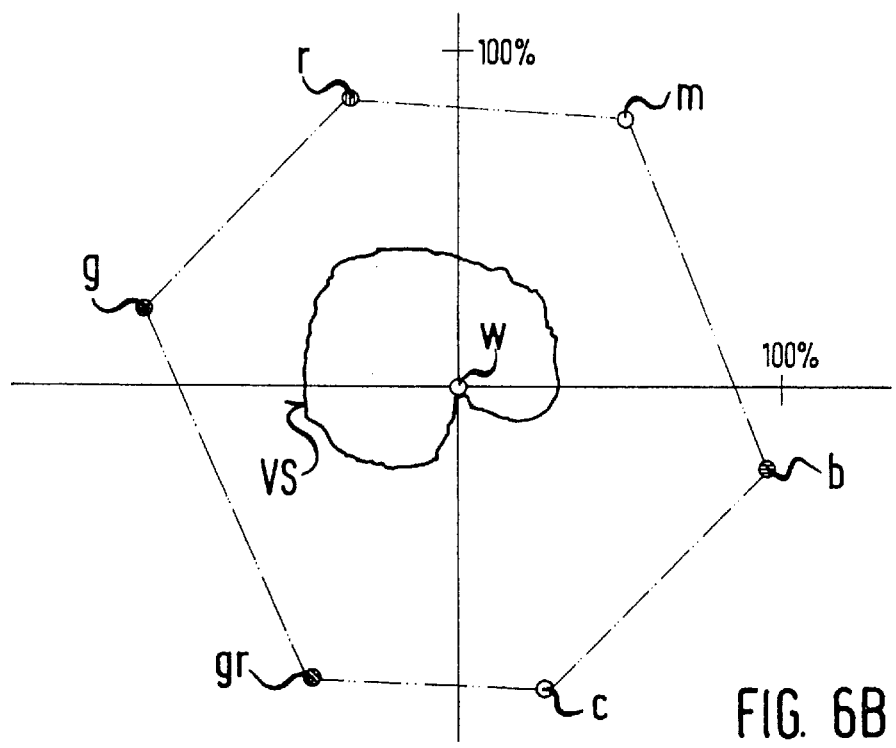
Figure 6C:
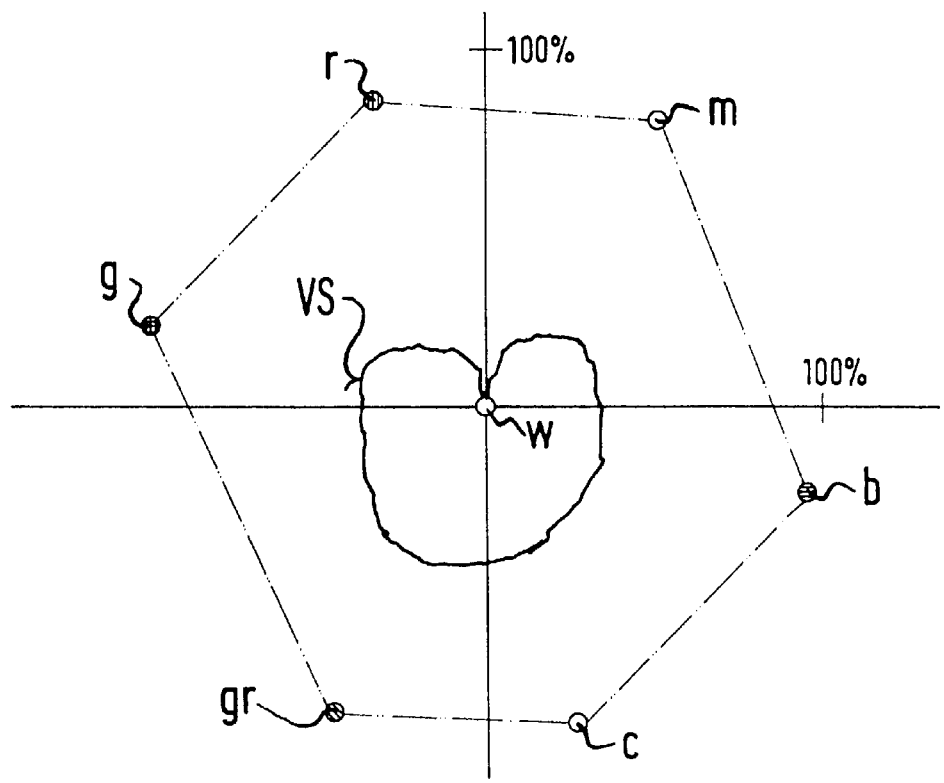

FIGS. 6A, 6B and 6C respectively show examples for characteristic adjusting curves for urology/arthroscopy, for minimal invasive surgery applications, and for use in ears, nose and throat applications whereby it must be noted that those characteristic adjusting curves given in FIGS. 6A to 6C are only examples and are set up on the basis of estimations. In these drawings the reference letters *w, r, g, gr, c, b* and *m* stand for white, red, yellow, green, cyano, blue and magenta in this corresponding order.

One can recognize that the color contrast with application in urology/arthroscopy according to FIG. 6A can be increased in the region of red, that in the application in minimal invasive surgery according to FIG. 6B apart from the red contrast the colors green and yellow may also be emphasized, and that finally in ear, nose and throat applications in FIG. 6C the color contrast in the green and cyano range may be increased. After a white balancing has taken place the correction value is located at the white point. The white point is still located on the adjusting curve and serves as a starting point. A correction value resulting after the correction has been carried out remains even after turning off the control device and is only set again to zero after renewed white balancing.

What is claimed is:

1. A device for correcting a tone of color pictures recorded by a video camera (1), the video camera comprising a converter (9) which converts a recorded picture into an electrical color picture signal, and a control device (3) to control the tone of the color picture which is displayed on a monitor (8), independently of the displayed color picture, the control device comprising a white balancing key and a function for automatic white balancing (AWB) upon actuation of the white balancing key by a user, and means for correcting tone values of ground colors, dependent on a selectably changeable correction value in accordance with at least one predetermined characteristic adjusting curve (VS) which determines a relationship between the tone values of the ground colors and chosen correction values which after carrying out the automatic white balancing, corrects the color tone values of the ground colors exclusively in accordance with a selected one of the at least one predetermined characteristic curve.

2. A device according to claim 1, characterized in that each characteristic adjusting curve (VS) is stored in tabular form in a memory and the control device (3) reads out the correction values from the memory on the basis of relevant input values.

3. A device according to claim 2, characterized in that several characteristic adjusting curves (VS), dependent on the type of endoscope light source employed, are stored in the memory and can be selected according to the case of application.

4. A device according to claim 1, characterized in that several characteristic adjusting curves (VS), dependent on the field of medical application, are stored in the memory and can be selected according to the case of application.

5. A device according to claim 1, characterized in that the control device (3) comprises an interface (6) for inputting and for reading in one or more characteristic adjusting curves (VS).

6. A device according to claim 1, characterized in that the characteristic adjusting curves (VS) represent the tone correction of only two ground colors and the third ground color is determined from these using a known additive color law.

7. A device according to claim 1, characterized in that a stop free transformer (1), operable by the user and rotatable about 360°, is connected to the control device (3) for inputting the correction values.

* * * * *